US00PP31984P2

(12) United States Plant Patent
Bak et al.

(10) Patent No.: US PP31,984 P2
(45) Date of Patent: Jul. 14, 2020

(54) ***GUZMANIA* PLANT NAMED 'CHIC'**

(50) Latin Name: ***Guzmania* sp.**
Varietal Denomination: CHIC

(71) Applicant: Corn Bak B.V., Assendelft (NL)

(72) Inventors: Elly Bak, Rijsenhout (NL); Nicolaas Steur, Oude Niedorp (NL)

(73) Assignee: Corn Bak BV (NL)

( * ) Notice: Subject to any disclaimer, the term of this patent is extended or adjusted under 35 U.S.C. 154(b) by 0 days.

(21) Appl. No.: 16/602,007

(22) Filed: Jul. 18, 2019

(51) Int. Cl.
*A01H 5/02* (2018.01)
*A01H 6/22* (2018.01)

(52) U.S. Cl.
USPC ..... Plt./371

(58) Field of Classification Search
USPC ..... Plt./263.1, 370, 371
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Guzmania* hybrid plant named 'CHIC' characterized by A solid growth habit; funnel-form rosette plant, measuring about 45 cm in height, green color foliage (measuring about 35 to 45 cm length and about 3.5 cm in width) and superior floral bract production. Bracts are red in color (closest to RHS 42A), compound inflorescence, measuring about 20 cm in height and about 20 cm in diameter; and long-lasting habit. The new variety is a *Guzmania*, typically produced as an indoor ornamental plant.

1 Drawing Sheet

Latin name of the genus and species: *Guzmania* sp.
Variety denomination: 'CHIC'.

BACKGROUND OF THE INVENTION

The present invention relates to a new and distinct hybrid cultivar of *Guzmania* plant, botanically known as *Guzmania* sp., of the family Bromeliaceae, and hereinafter referred to as 'CHIC'. *Guzmania* is native to tropical America. *Guzmania* is predominantly epiphytic with a few terrestrial species and is native to the tropics. For the most part, species vary in diameter from 7 or 8 inches to 3 or 4 feet and have rosettes of glossy, smooth-edged leaves. Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived. *Guzmania* may be advantageously grown as pot plants for greenhouse or home use. Typically, the plants are shaded from direct sunlight. During the spring to autumn period, the central vase-like part of the leaf rosette is normally filled with water.

The new *Guzmania* 'CHIC' originated from a cross made in a controlled breeding program by the inventors in 2005. The female or seed parent is the unnamed *Guzmania* selection identified by code 05062520 (unpatented). The male or pollen parent is the unnamed *Guzmania* selection identified by code 05062582 (unpatented). The new *Guzmania* 'CHIC' was discovered and selected by the inventors in 2009 as a single flowering plant within the progeny of the stated cross in a controlled environment in Assendelft, The Netherlands.

Asexual reproduction of the new *Guzmania* cultivar was first performed by off-shoots beginning in 2010 and then by tissue culture beginning in 2015 in Assendelft, The Netherlands, with first flowering after asexual reproduction occurring in 2019 in Assendelft, The Netherlands. Asexual reproduction of the *Guzmania* 'CHIC' has demonstrated that the combination of characteristics as herein disclosed for the new cultivar are firmly fixed and retained through successive generations of asexual reproduction. The new cultivar reproduces true to type.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

SUMMARY OF THE INVENTION

The following traits have been repeatedly observed and are determined to be unique characteristics of 'CHIC' which in combination distinguish this *Guzmania* as a new and distinct cultivar:

1. Solid growth habit.
2. Funnel-form rosette plant, measuring about 45 cm in height (above the pot when flowering).
3. Numerous, green colored foliage, measuring about 42 cm in length and about 3.5 cm in width.
4. Superior floral bract production.
5. Unique red inflorescence (RHS 42A).
6. Compound inflorescence, measuring from about 20 cm in height and about 20 cm in diameter.
7. Long-lasting habit.

PARENTAL COMPARISON

Plants of the parental *Guzmania* selection identified by code 05062520 and *Guzmania* selection identified by code 05062582 (both unpatented) are no longer available to provide a botanical comparison with the new *Guzmania* hybrid 'CHIC'.

COMMERCIAL COMPARISON

Of the many commercial cultivars known to the present inventors, the most similar in comparison to the new *Guzmania* hybrid 'CHIC' is the *Guzmania* 'FUTURA', U.S. Utility Pat. No. 9,439,372. Plants of the new hybrid 'CHIC' differ from plants of 'FUTURA' primarily in the following characteristics:

1. Plants of 'CHIC' produce floral bracts which are red with white in color and visible present whereas plants of 'FUTURA' produce floral bracts which are enclosed within the inflorescence.
2. Plants of 'CHIC' produce primary bracts that are moderately recurved whereas plants of 'FUTURA' produce primary bracts are strongly recurved.

BRIEF DESCRIPTION OF THE PHOTOGRAPH

The accompanying photograph illustrate the overall appearance of the new *Guzmania* hybrid 'CHIC' showing the colors as true as is reasonably possible with colored reproductions of this type. Colors in the photograph may differ slightly from the color values cited in the detailed botanical description which accurately describes the color of 'CHIC'. The accompanying figure shows a side view perspective of the primary and top bracts produced by a typical potted, flowering plant of 'CHIC', at 13 months of age from potting size.

DETAILED BOTANICAL DESCRIPTION

'CHIC' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant. For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant. The aforementioned photographs, together with the following observations, measurements and values describe the new *Guzmania* 'CHIC' as grown in a greenhouse in Assendelft, The Netherlands, under conditions which closely approximate those generally used in commercial practice. Plants of 'CHIC' were grown in a greenhouse with day temperatures ranging from 20° C. to 28° C. and night temperatures ranging from 18° C. to 23° C. No artificial lighting or photoperiodic treatments were conducted, but plants of 'CHIC' are forced into flowering. The following fertilizer is added when growing plants of 'CHIC': 1 part nitrogen, 0.6 parts phosphor, 2 parts Kalium and 0.1 parts magnesium. Color references are made to The Royal Horticultural Society Colour Chart (R.H.S.), 2001 edition, except where general colors of ordinary significance are used. Color values were taken under daylight conditions in a greenhouse in Assendelft, The Netherlands. The age of the plants of 'CHIC' described is about 17 weeks after flowering treatment.

Botanical classification: *Guzmania* hybrid.

Plant:

*Height*.—About 45 cm (when flowering).
*Width*.—About 60 cm.
*Shape*.—Funnel form rosette.
*Growth habit*.—Stemless.
*Plant vigor*.—Moderate.
*Flowering season*.—A fully grown plant can flower year-round, starting 17 weeks after induction of natural light or through flowering treatment.
*Cold tolerance*.—Frost tender. Temperatures below 5° C. may damage plants.
*Fragrance*.—None.

Foliage:

*Quantity*.—About 15 (depending on the size of the plant).
*Size of leaf*.—Length: About 42 cm (when flowering). Width: About 3.5 cm.
*Overall shape*.—Linear-lanceolate.
*Apex shape*.—Acuminate.
*Base shape*.—Strap-like around central axis.
*Margin*.—Entire.
*Texture* (*both surfaces*).—Smooth.
*Orientation*.—Leaf blades arch continuously from base.
*Color*.—Leaf color can vary somewhat depending on growing conditions. Mature: Upper surface: RHS Green 137A with anthocyanin stripes, closest to RHS Greyed-Purple 187A. Under surface: RHS Green 137A with anthocyanin stripes, closest to RHS Greyed-Purple 187A. Immature: Upper surface: RHS Green 137A. Under surface: RHS Green 137A.
*Venation*.—None.

Inflorescence:

*Borne*.—Erect stalks.
*Shape*.—Compound.
*Size*.—Length: About 45 cm. Diameter: About 20 cm.
*Time of bloom*.—A fully grown plant can produce an inflorescence containing about 120 flowers (depending on the size of the plants), and can bloom the whole year starting about 17 weeks after natural induction or through flowering treatment.
*Duration of bloom*.—Each flower blooms one (1) day.

Flowers: Not visible during anthesis.

Petals:

*Number*.—3 per flower.
*Length*.—About 3 cm.
*Width*.—About 0.6 cm.
*Overall shape*.—Ligulate.
*Apex shape*.—Obtuse.
*Base shape*.—Fused.
*Color*.—Upper and Under surfaces: RHS White 155D.

Sepals:

*Number*.—3 per flower.
*Length*.—About 3 cm.
*Width*.—About 0.5 cm.
*Overall shape*.—Ligulate.
*Apex shape*.—Acute.
*Base shape*.—Sessile.
*Color*.—Translucent.

Bracts:

Scape bracts:

*Quantity*.—About 10.
*Arrangement*.—Alternate.

*Size*.—Length: About 28 cm (lowest) to about 12 cm (scape bracts positioned just below the primary bracts). Width: About 4 cm.

*Overall shape*.—Lanceolate.

*Apex shape*.—Acute.

*Base shape*.—Fused.

*Margin*.—Entire.

*Texture*.—Smooth.

*Color*.—Upper surface: RHS Green 137A with Red 42A, and Greyed-Purple 187A. Under surface: RHS Green 137A with Red 42A, and Greyed-Purple 187A.

Primary bracts:

*Quantity*.—About 18.

*Arrangement*.—Alternate.

*Size*.—Length: About 12 cm. Width: About 4.5 cm.

*Overall shape*.—Lanceolate.

*Apex shape*.—Acute.

*Base shape*.—Fused.

*Margin*.—Entire.

*Texture*.—Smooth.

*Color*.—Upper and Under surfaces: RHS Red 42A.

Floral bracts:

*Quantity*.—About 120.

*Size*.—Length: About 5 cm. Width: About 1.7 cm.

*Overall shape*.—Lanceolate.

*Apex shape*.—Obtuse.

*Base shape*.—Fused.

*Margin*.—Entire.

*Texture*.—Smooth.

*Color*.—Upper and Under surfaces: RHS Red 43A with White 155D. Upper and Under surfaces: RHS Red 43A with White 155D.

Reproductive organs:

Androecium:

*Stamen*.—Number: 6 per flower. Length: About 2 cm. Diameter: About 1 mm. Color: RHS White 155D.

*Anther*.—Length: About 0.6 cm. Color: RHS Yellow-White 158B.

Pollen: None.

Gynoecium:

*Pistil*.—Number: 1 per flower. Length: About 3.2 cm.

*Stigma*.—Shape: 3-parted. Width: About 2 mm. Color: White, (too small to qualify R.H.S. value).

*Style*.—Length: About 2.2 cm. Color: White (too small to qualify R.H.S. value).

*Ovary*.—Position: Superior. Shape: Conical. Length: About 1 cm. Diameter: About 0.3 cm. Color: RHS Yellow-Green 145C.

Other characteristics:

Seeds/fruit: Sterile hybrid, therefore, no seed or fruit produced.

Disease/pest resistance: No observations made.

Disease/pest susceptibility: No observations made.

What is claimed is:

1. A new and distinct cultivar of *Guzmania* plant named 'CHIC' as herein illustrated and described.

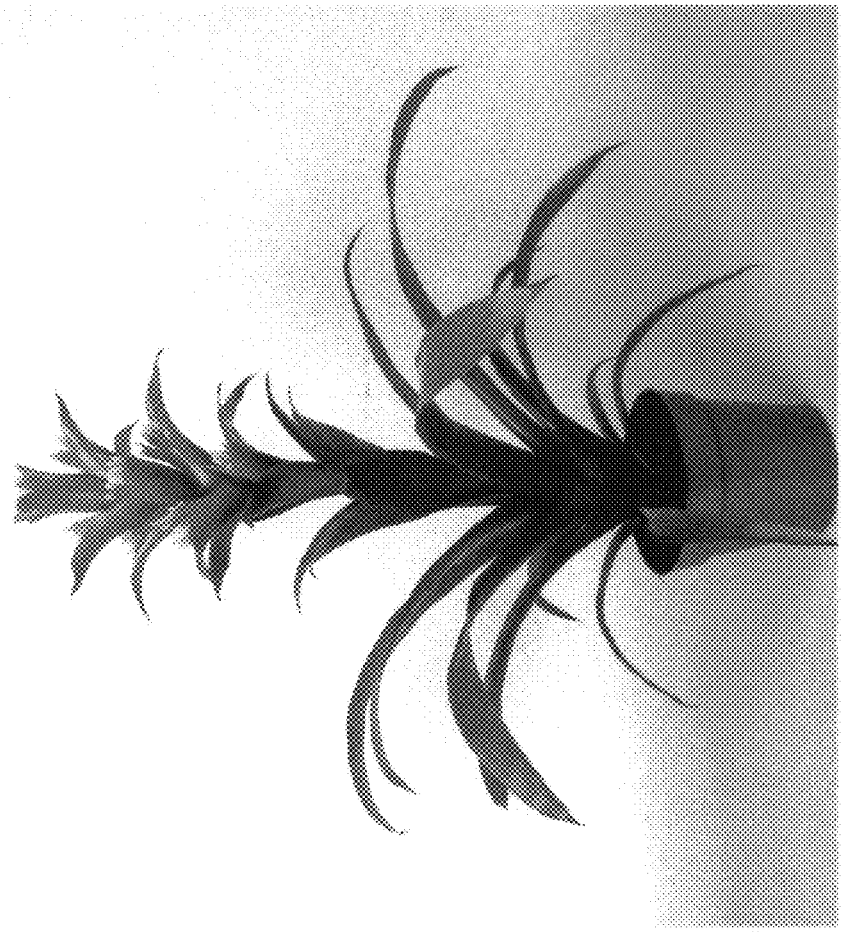

* * * * *